(12) United States Patent
Requarth

(10) Patent No.: US 9,332,990 B2
(45) Date of Patent: *May 10, 2016

(54) URETER TO ILEAL CONDUIT ANASTOMOSIS USING MAGNETIC COMPRESSION AND RELATED DELIVERY DEVICES AND METHODS

(75) Inventor: Jay Anthony Requarth, Winston-Salem, NC (US)

(73) Assignee: WAKE FOREST UNIVERSITY HEALTH SCIENCES, Winston-Salem, NC (US)

( * ) Notice: Subject to any disclaimer, the term of this patent is extended or adjusted under 35 U.S.C. 154(b) by 176 days.

This patent is subject to a terminal disclaimer.

(21) Appl. No.: 13/334,159

(22) Filed: Dec. 22, 2011

(65) Prior Publication Data

US 2012/0197062 A1 Aug. 2, 2012

Related U.S. Application Data

(60) Provisional application No. 61/428,466, filed on Dec. 30, 2010.

(51) Int. Cl.
| | |
|---|---|
| *A61B 17/11* | (2006.01) |
| *A61N 2/10* | (2006.01) |
| *A61N 5/10* | (2006.01) |
| *A61B 17/00* | (2006.01) |
| *A61B 17/22* | (2006.01) |
| *A61M 25/01* | (2006.01) |
| *A61M 25/04* | (2006.01) |
| *A61M 25/10* | (2013.01) |

(52) U.S. Cl.
CPC .............. *A61B 17/11* (2013.01); *A61N 5/1001* (2013.01); *A61B 2017/00876* (2013.01); *A61B 2017/1135* (2013.01); *A61B 2017/1139* (2013.01); *A61B 2017/22065* (2013.01); *A61M 25/0127* (2013.01); *A61M 25/04* (2013.01); *A61M 25/1011* (2013.01)

(58) Field of Classification Search
CPC ............... A61B 17/11; A61B 17/1114; A61B 2017/1117; A61B 2017/1135; A61B 2017/1139; A61B 2017/00876; A61B 2019/464; A61M 25/10; A61M 25/1011; A61M 2025/1013
USPC ................................. 606/153, 151; 600/2, 12
See application file for complete search history.

(56) References Cited

U.S. PATENT DOCUMENTS

| | | | |
|---|---|---|---|
| 5,690,656 A | 11/1997 | Cope et al. | |
| 5,779,694 A | 7/1998 | Howard et al. | |
| 6,059,714 A * | 5/2000 | Armini et al. | 600/3 |
| 6,352,543 B1 * | 3/2002 | Cole | 606/153 |

(Continued)

OTHER PUBLICATIONS

Volchok and Kulp, Half-Life of Yttrium-90, Jan. 1, 1955, Physical Review, vol. 97, No. 1.*

(Continued)

*Primary Examiner* — Todd J Scherbel
(74) *Attorney, Agent, or Firm* — Myers Bigel & Sibley, P.A.

(57) ABSTRACT

Magnetic compression anastomosis can be carried out by placing cooperating magnets, one in the ileal conduit and one in the ureter, to lock together and form the anastomosis. The magnets may be placed to form a side-to-side anastomosis. At least one of the magnets can include radioactive material. Catheters may be used to place the magnets, and the catheters may have at least one deflatable or retractable tissue spacer.

31 Claims, 9 Drawing Sheets

(56) References Cited

U.S. PATENT DOCUMENTS

| | | | |
|---|---|---|---|
| 6,585,632 B2* | 7/2003 | Vallana et al. ............... 600/3 |
| 6,632,229 B1* | 10/2003 | Yamanouchi ............. 606/153 |
| 6,652,540 B1 | 11/2003 | Cole et al. |
| 6,802,847 B1 | 10/2004 | Carson et al. |
| 6,932,827 B2 | 8/2005 | Cole |
| 7,232,449 B2 | 6/2007 | Sharkawy et al. |
| 7,344,490 B2* | 3/2008 | Shaw et al. ............... 600/3 |
| 7,387,636 B2 | 6/2008 | Cohn et al. |
| 7,431,727 B2 | 10/2008 | Cole et al. |
| 7,771,442 B2 | 8/2010 | Shriver |
| 7,879,051 B2 | 2/2011 | Swain et al. |
| 2003/0229363 A1* | 12/2003 | Sharkawy et al. ............. 606/153 |
| 2004/0186514 A1 | 9/2004 | Swain et al. |
| 2005/0080439 A1* | 4/2005 | Carson et al. ............... 606/153 |
| 2005/0113851 A1 | 5/2005 | Swain et al. |
| 2006/0052759 A1* | 3/2006 | Johansson et al. ............ 604/277 |
| 2009/0048618 A1* | 2/2009 | Harrison et al. ............. 606/153 |
| 2009/0227828 A1* | 9/2009 | Swain et al. ................... 600/12 |
| 2009/0322323 A1* | 12/2009 | Brazdeikis et al. ........... 324/244 |
| 2010/0004661 A1* | 1/2010 | Verin et al. ................... 606/129 |
| 2010/0179510 A1* | 7/2010 | Fox et al. ...................... 604/509 |
| 2010/0256659 A1* | 10/2010 | Aguirre et al. ............... 606/153 |
| 2010/0292729 A1* | 11/2010 | Aguirre et al. ............... 606/213 |
| 2011/0144560 A1 | 6/2011 | Gagner et al. |

OTHER PUBLICATIONS

Avaliani et al., Magnetic Compression Biliary-enteric Anastomosis for Palliation of Obstructive Jaundice: Initial Clinical Results, J Vasc Interv Radiol, 2009, pp. 614-623, vol. 20, No. 5.

Giovannini et al., Endoscopic Ultrasound-Guided Bilioduodenal Anastomosis: A New Technique for Biliary Drainage, Endoscopy, 2001, pp. 898-900, vol. 33, No. 10, Abstract.

Hanada et al., Endoscopic ultrasound-guided choledochoduodenostomy for palliative biliary drainage in cases with inoperable pancreas head carcinoma, Digestive Endoscopy, 2009, pp. S75-S78, vol. 21, Suppl. 1.

Paik et al., Palliative treatment with self-expandable metallic stents in patients with advanced type III or IV hilar cholangiocarcinoma: a percutaneous versus endoscopic approach, Gastrointestinal Endoscopy, Jan. 2009, pp. 55-62, vol. 69, No. 1, Abstract.

USPTO Office Action for pending U.S. Appl. No. 13/334,532, filed Dec. 22, 2011, Mail Date Apr. 9, 2014, 26 pages.

Yamamoto et al., A new method of enteroscopy—the double-balloon method, Can. J. Gastroenterol, Apr. 2003, pp. 273-274, vol. 17, No. 4, Abstract and as provided by Office Action in U.S. Appl. No. 13/334,532.

* cited by examiner

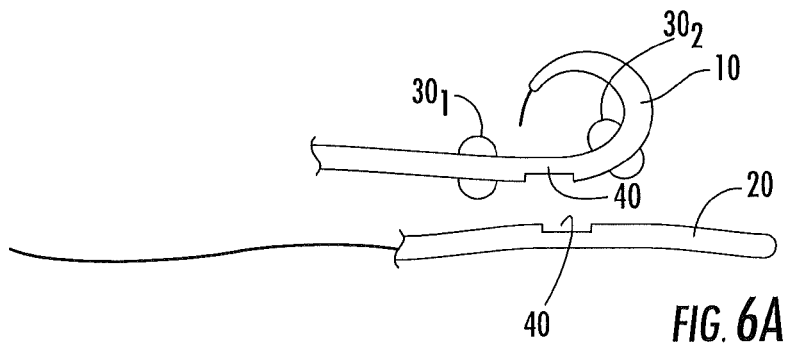
FIG. 6A
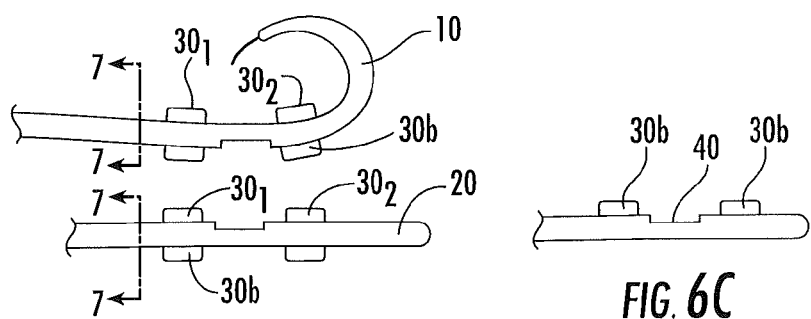
FIG. 6B
FIG. 6C
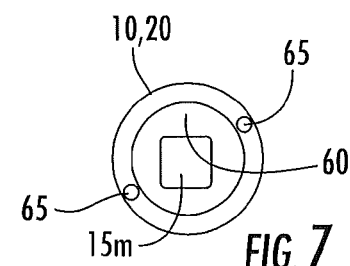
FIG. 7
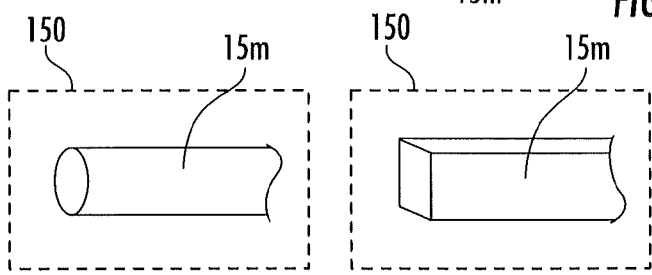
FIG. 8
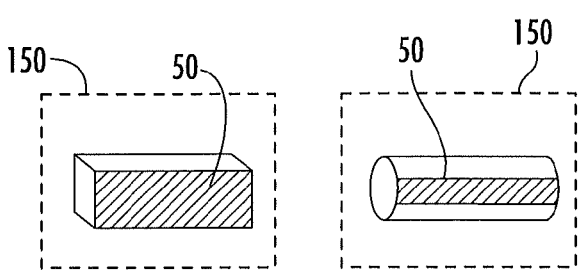
FIG. 9

URETER TO ILEAL CONDUIT ANASTOMOSIS USING MAGNETIC COMPRESSION AND RELATED DELIVERY DEVICES AND METHODS

RELATED APPLICATIONS

This application claims the benefit of and priority to U.S. Provisional Application Ser. No. 61/428,466, filed Dec. 30, 2010, the contents of which are hereby incorporated by reference as if recited in full herein.

FIELD OF THE INVENTION

This invention relates to surgical devices that may be particularly useful for forming anastomosis between two hollow viscera using magnets.

BACKGROUND OF THE INVENTION

Ureteral strictures commonly occur after cystectomies (which is often used to treat patients with bladder cancer), particularly after robotic surgery. Unfortunately, conventional repairs involve relatively lengthy surgeries. There remains a need for alternate ways to form primary and redo anastomosis in patients having ileal conduits.

SUMMARY OF EMBODIMENTS OF THE INVENTION

Embodiments of the invention are directed to devices and methods for forming a magnetic compression anastomosis between the ureter and the ileal conduit.

Some embodiments are directed to methods of forming an anastomosis. The methods include: (a) placing a first magnet in a ureter of a patient proximate an ileal conduit; (b) placing a second magnet in the ileal conduit of a patient proximate the ureter; and (c) compressing tissue trapped between the first and second magnets based on a magnetic attraction force generated by the magnets, the compressing performed with sufficient force to form an anastomosis.

The placing steps can be carried out to create a side-to-side anastomosis upstream of an original anastomosis or a sutured end of the ureter.

At least one of the first and second magnets may optionally include a radioactive material. The method can further include exposing the trapped tissue to radiation from the at least one magnet. The forming step can be carried out based on the locking and the exposing steps.

In some embodiments, at least one of the placing the first magnet or the placing the second magnet is carried out using a catheter with a tissue spacer. At least one of the placing steps can include retracting or deflating the tissue spacer from an extended or inflated configuration prior to the magnet contacting local tissue.

Optionally, the steps of placing the first and second magnets can be carried out using respective catheters, at least one of the catheters having a magnet exit window with at least one inflatable tissue spacer proximate the window. Thus, the method can further include deflating the tissue spacer to position the ureter side or ileal conduit side magnet in alignment with the other magnet.

Still other embodiments are directed to ureter catheters. The ureter catheters include a catheter body sized and configured to travel through a ureter of a patient. The catheter body has an inner channel and an outer wall enclosing the inner channel. The ureter catheters also include a rare earth magnet releasably held in the catheter body adapted for positioning in a distal end of the ureter proximate an ileal conduit.

The catheter may optionally include window is a longitudinally extending window extending through the outer wall having opposing first and second ends extending a defined length of the catheter body configured to place the magnet on a sidewall of the ureter facing the ileal conduit to form a side-to-side anastomosis.

Yet other embodiments are directed to ileal conduit catheters. The ileal conduit catheters include a catheter body sized and configured to travel through a stoma and a distance through an illeat conduit of a patient. The catheter body has an inner channel and an outer wall enclosing the inner channel and a rare earth magnet releasably held in the catheter body adapted for positioning in a the ileal conduit proximate a ureter.

The catheter body can include a longitudinally extending window extending through the outer wall having opposing first and second ends extending a defined length of the catheter body.

The catheter body can also include a first tissue spacer proximate the first end of the window and a second tissue spacer proximate the second end of the window.

The ureter or ileal conduit catheters can include at least one inflatable tissue spacer, typically a first inflatable tissue spacer proximate one end of the window and a second inflatable tissue spacer proximate an opposing longitudinal end of the window.

The rare earth magnets can include neodymium.

In some embodiments, the magnet includes a radioactive material. The radioactive material may be a beta emitter having a half-life that is between about 24 to about 120 hours, more typically about 48 hours. The radioactive material can include Yttrium-90.

The ureter and/or ileal conduit catheters can include a magnetic force sensor on the catheter body proximate a magnet exit window.

Still other embodiments are directed to delivery systems for placing ureter and ileal conduit magnets for generating magnetic compression. The systems include: (a) a ureter catheter having a magnet held therein for percutaneous delivery to a ureter then to a distal end of the ureter; and (b) an ileal conduit catheter having a magnet held therein for delivery to a target intrabody site. The ureter and ileal conduit catheters deliver respective magnets to cooperate and lock together on opposing sides of tissue and generate magnetic compression on trapped tissue.

The ureter catheter and the ileal conduit catheter can be configured to generate a side-to-side anastomosis using a portion of the ureter that is upstream of the distal end thereof but relatively close to an end portion of the cut ureter (the caudal end).

The system can also include a control circuit in communication with the ureter and/or ileal conduit catheter configured to carry out at least one of the following: (a) monitor magnetic force data sensed by a sensor on the ureter and/or ileal conduit catheters; or (b) generate an alert when magnetic force is detected to be insufficient.

The ureter and ileal conduit catheters may each comprise a magnet exit window on a side or tip portion thereof, and wherein at least one of the ureter or ileal conduit catheters comprises spaced apart first and second inflatable tissue spacers proximate the window.

In some embodiments, at least one of the magnets of the first and second catheter comprises a radioactive material.

The radioactive material may optionally include a beta emitter. At least one of the magnets may also include a string attached to the magnet.

Some embodiments are directed to delivery systems for placing intrabody magnets for generating magnetic compression. The systems include: (a) a first catheter having a magnet held therein; and (b) a second catheter having a magnet held therein for delivery to a target intrabody site. The first and second catheters deliver respective magnets to cooperate and lock together on opposing sides of tissue and generate magnetic compression on trapped tissue. The systems also include a control circuit in communication with the first and/or second catheter, configured to: (a) monitor magnetic force data sensed by a sensor on the first and/or second catheters; and (b) generate an alert when the monitored magnetic force is detected to be insufficient and/or sufficient.

The foregoing and other objects and aspects of the present invention are explained in detail in the specification set forth below.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

BRIEF DESCRIPTION OF THE DRAWINGS

FIG. 6A is a schematic illustration of alternate configurations of catheters according to embodiments of the present invention.

FIG. 6B is a schematic illustration of yet other alternate configurations of catheters according to embodiments of the present invention.

FIG. 6C is a schematic illustration of an additional configuration of a catheter according to embodiments of the present invention.

FIG. 7 is a sectional view taken along line 7-7 in FIG. 6B according to embodiments of the present invention.

FIG. 8 is a front perspective view of exemplary magnets that can be placed in the body using catheters according to embodiments of the present invention.

FIG. 9 is a front perspective view of exemplary magnets with a radioactive material according to embodiments of the present invention.

DESCRIPTION OF EMBODIMENTS OF THE INVENTION

Figure 1:
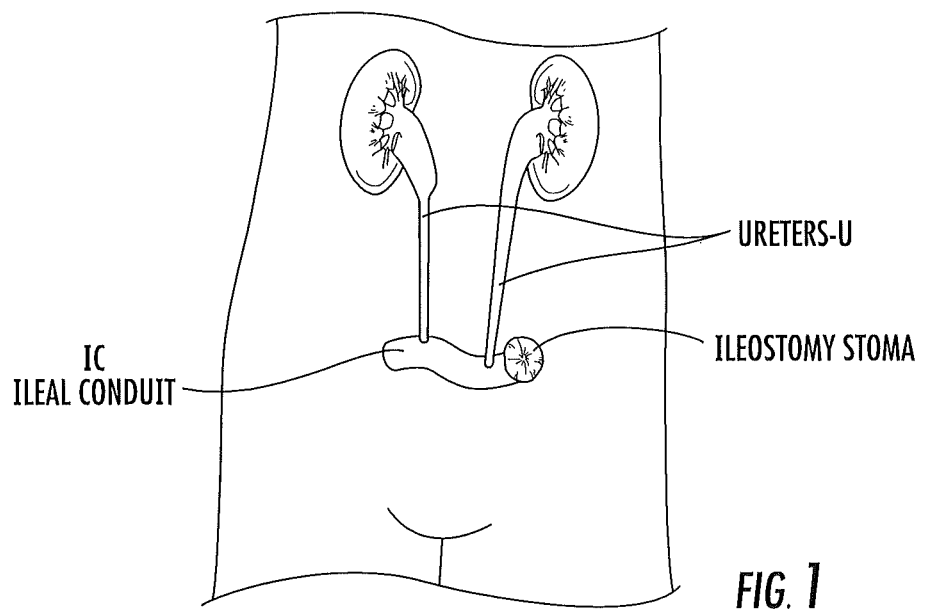
FIG. 1 is a schematic illustration of a patient with an ileal conduit.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. In the drawings, the thickness of lines, layers, features, components and/or regions may be exaggerated for clarity and broken lines illustrate optional features or operations, unless specified otherwise.

The terminology used herein is for the purpose of describing particular embodiments only and is not intended to be limiting of the invention. As used herein, the singular forms, "a", "an" and "the" are intended to include the plural forms as well, unless the context clearly indicates otherwise. It will be further understood that the terms "comprises," "comprising," "includes," and/or "including" when used in this specification, specify the presence of stated features, regions, steps, operations, elements, and/or components, but do not preclude the presence or addition of one or more other features, regions, steps, operations, elements, components, and/or groups thereof.

It will be understood that when a feature, such as a layer, region or substrate, is referred to as being "on" another feature or element, it can be directly on the other feature or element or intervening features and/or elements may also be present. In contrast, when an element is referred to as being "directly on" another feature or element, there are no intervening elements present. It will also be understood that, when a feature or element is referred to as being "connected", "attached" or "coupled" to another feature or element, it can be directly connected, attached or coupled to the other element or intervening elements may be present. In contrast, when a feature or element is referred to as being "directly connected", "directly attached" or "directly coupled" to another element, there are no intervening elements present. Although described or shown with respect to one embodiment, the features so described or shown can apply to other embodiments.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein.

Embodiments of the invention are useful for veterinarian and human uses as well as for animal studies. That is, methods and devices provided by embodiments of the invention can be configured for any species of interest, e.g., mammalian including human, simian, mouse, rat, lagomorph, bovine, ovine, caprine, porcine, equine, feline, canine, and the like.

Embodiments of the invention may be particularly suitable for treating strictures or obstructions in ureters using percutaneous placement of the ureter magnet without requiring general anesthesia.

The term "catheter" refers to a flexible tube insertable into the body. The term "fluid" includes gases and liquids. The term "string" is used broadly and refers to a length of a biocompatible (sterile) thin flexible material formed of any suitable material or combinations of materials and may be in the form of a suture, thread, metallic and/or textile strip, filament, strand, braid or the like. The term "locking" refers to the engagement of the first and second magnets based on the magnetic attraction forces generated by the cooperating magnets.

FIG. 1 illustrates a patient with an ileal conduit ("IC") that leads to a stoma for the diversion of urinary flow from the ureters ("U") to an external collection device. As is well known, the ileal conduit is typically formed using dissected (detached) ileum and forms a surgical anastomosis of the ureters (or a bowel segment) to one end of the detached ileum. One end of the detached ileum is (sutured, stapled or otherwise) closed and the other is drawn through the abdominal wall to create a stoma. The patient typically wears a collection pouch to collect the urine.

Figure 2:
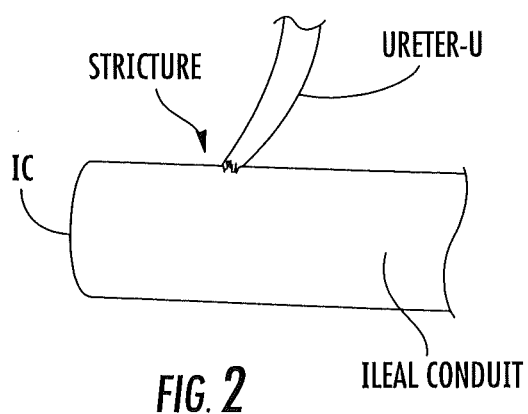
FIG. 2 is a schematic illustration of a stricture at the end of the ureter blocking the anastomosis.
Figure 3A:
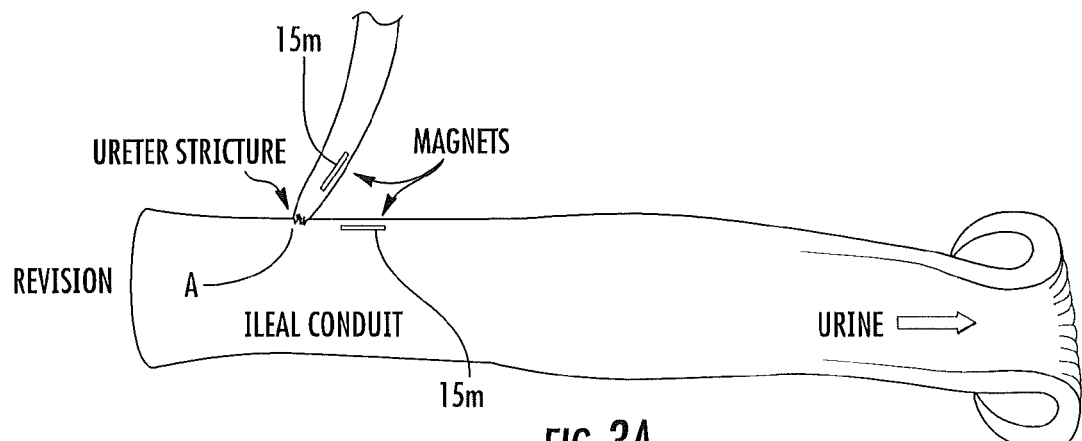
FIGS. 3A-3C are schematic illustrations of a pair of cooperating magnets that together apply magnetic compression to create an anastomosis or clear a stricture according to embodiments of the present invention.
Figure 3B:
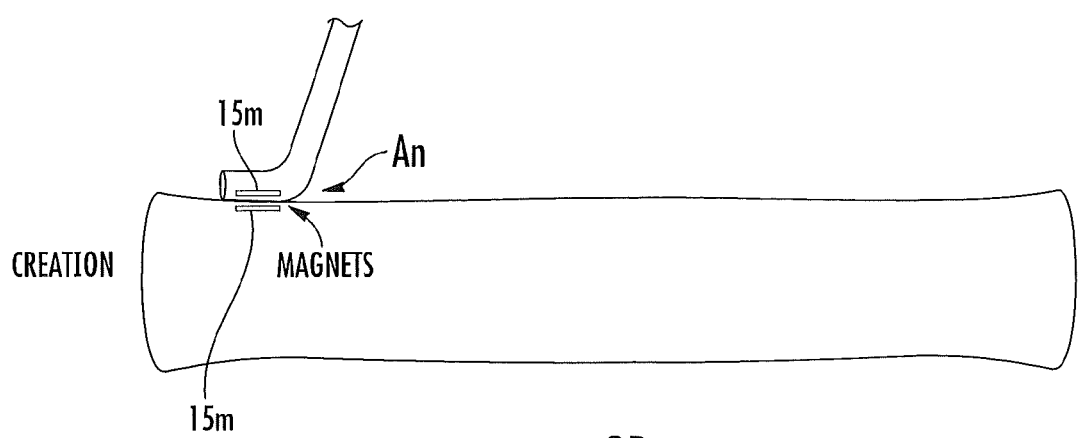
Figure 3C:
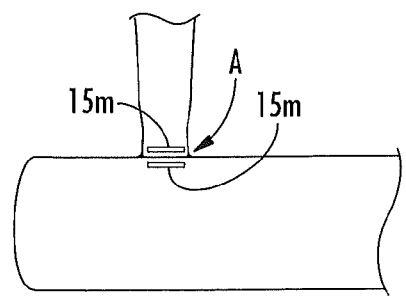

FIG. 2 illustrates that a stricture may form at the junction of the ureter and ileum conduit. Conventionally, surgical repair of this type of stricture can be time-consuming (sometimes taking up to about eight hours) and expensive. FIGS. 3A and 3B illustrate the creation of an alternate (primary) anastomosis "An" using a pair of magnets $15m$, one in the ureter U and one in the ileal conduit IC. As shown, the magnets $15m$ can be deployed to create a side-to-side antastomosis "An" using tissue of the ureter that is upstream of the original junction (but close to a caudal end of a cut ureter), rather than open the existing anastomosis. However, FIG. 3C illustrates that the magnets $15m$ may cooperate to open the ureter stricture at the original anastomosis "A" without requiring a "new" anastomosis "An." Yet other embodiments contemplate forming an original anastomosis using magnet pairs.

Figure 4A:
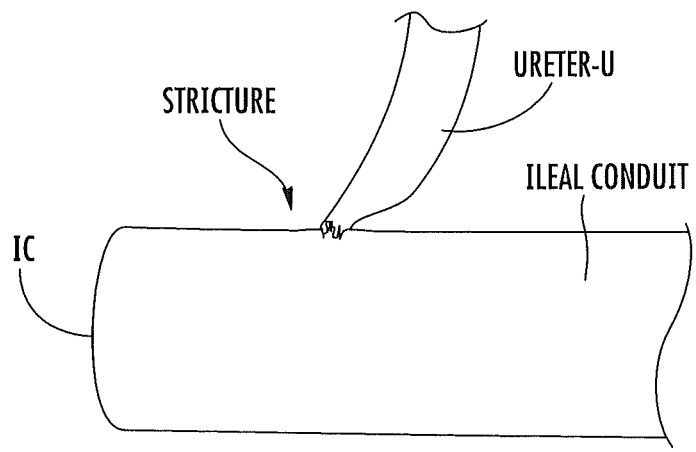
FIGS. 4A-4E are schematic illustrations of exemplary steps to place magnets in the ureter and ileal conduit using cooperating catheters according to embodiments of the present invention.
Figures 4B, 4C:
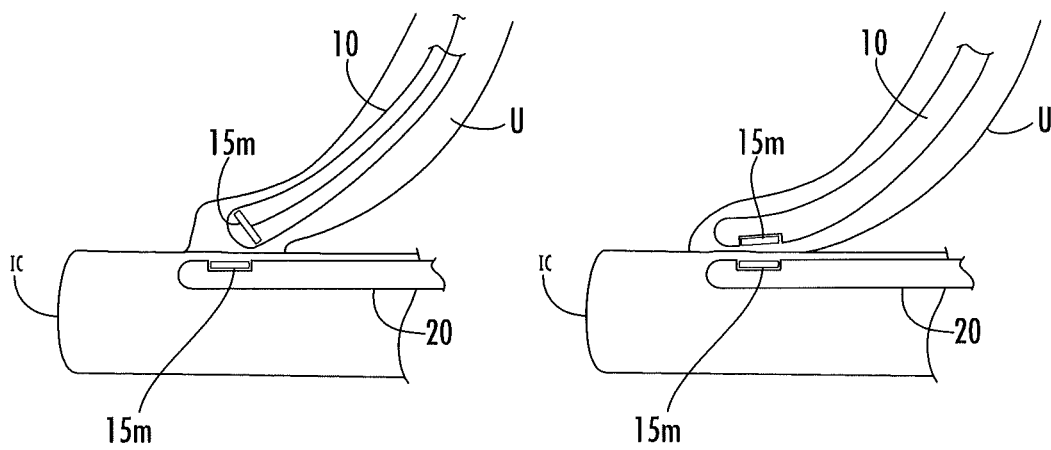
Figures 4D, 4E:
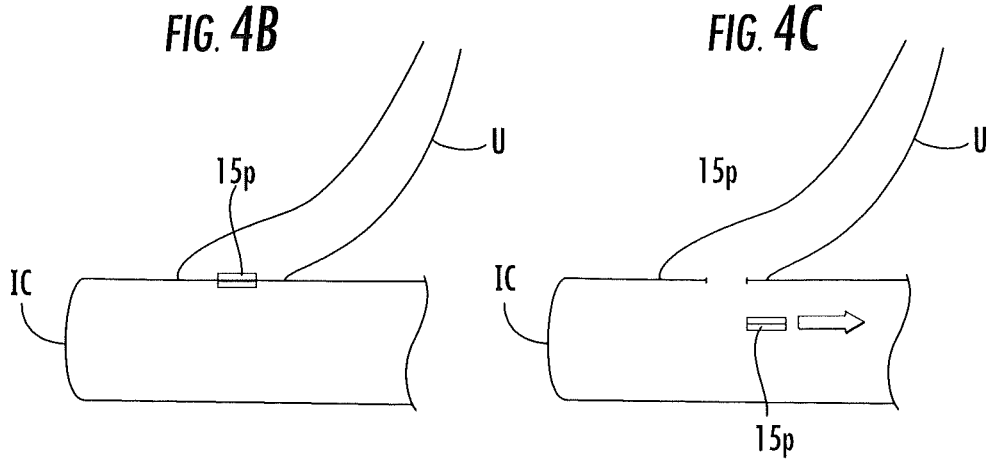

FIGS. 4A-4E illustrate an overview of magnet placement using catheters 10, 20. FIG. 4B illustrates that the ureter catheter 10 can hold the magnet $15m$ at a distal end portion thereof so that it exits the tip. FIG. 4C illustrates that the catheter 10 holds the magnet at a distal end portion but deploys the magnet out a side portion thereof. FIG. 4D illustrates the magnets in cooperating alignment, one in the ureter and the other in the ileal conduit, to provide ischemic compression of tissue therebetween. FIG. 4E illustrates that the magnet pair $15p$ can be discharged from the body with the flow of urine after the anastomosis is formed.

The catheters 10, 20 may comprise deflectable (steerable) shafts and end portions that allow the desired placement of the magnet in the body. The catheters 10, 20 may be placed using local anesthesia. The catheter 10 in the ureter U can be placed percutaneously using a conventional needle-guidewire-catheter configuration. Either or both catheters 10, 20 can be positioned using fluoroscopy and/or ultrasound or another imaging modality. The catheters can place the magnets using robotic or conventional means.

Figure 5:
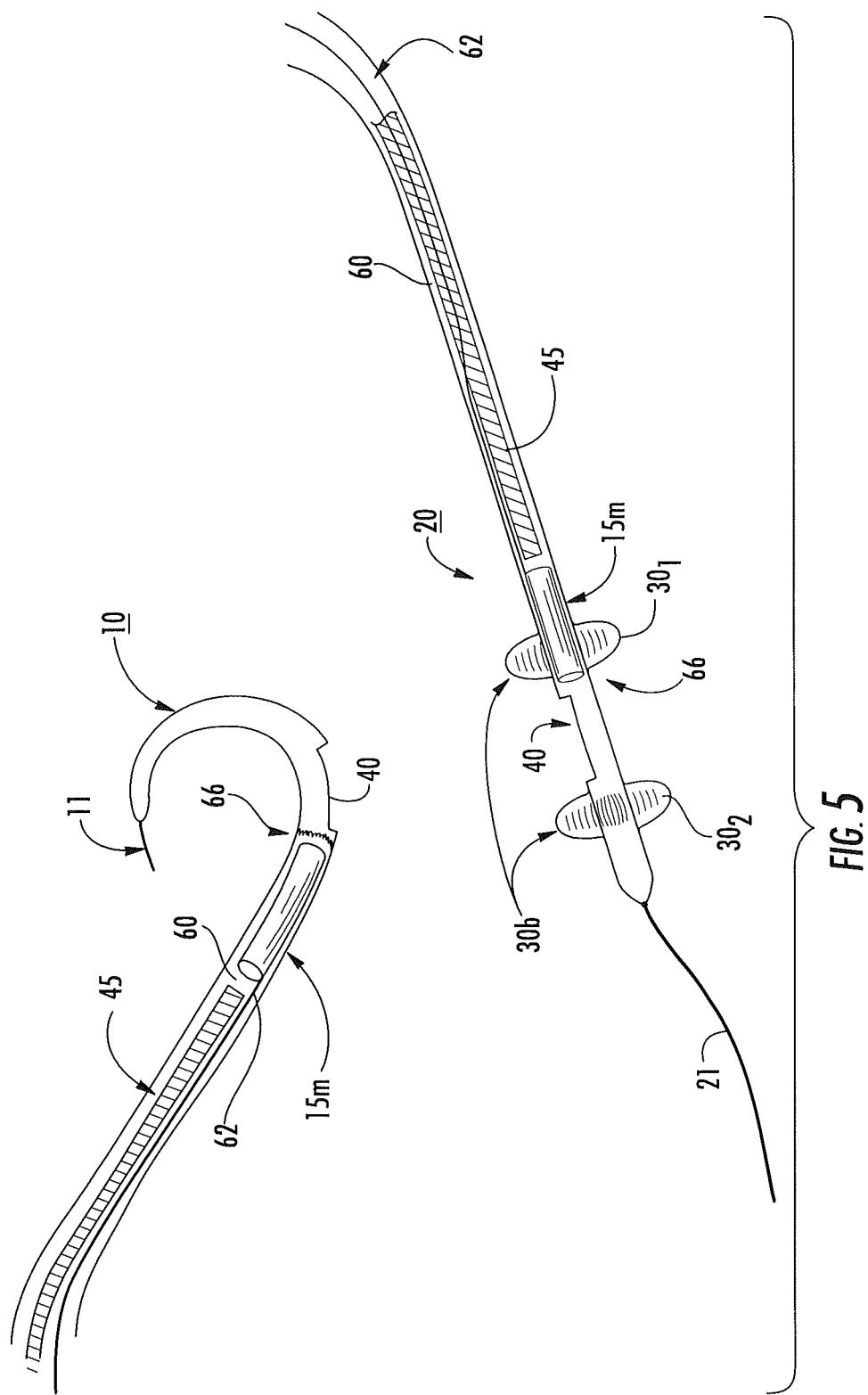
FIG. 5 is a schematic illustration of a pair of catheters that may be used to place the magnets according to embodiments of the present invention.

FIG. 5 shows two exemplary catheters 10, 20. The first catheter 10 is shown with a guidewire 11 and a deformable distal end as well as a side exit window 40. However, other catheter configurations may be used and may not include a guidewire. Similarly, although catheter 20 is shown as having a guidewire 11, it may have other configurations and be used without any guidewire.

Figure 16:
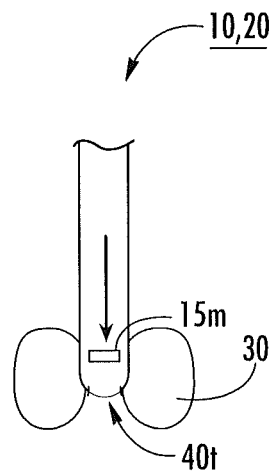
FIG. 16 is a schematic illustration of a catheter configured to deploy a magnet via the tip and having tip-end inflatable tissue spacer according to embodiments of the present invention.

As also shown in FIG. 5, at least one catheter 10, 20 (shown as the catheter 20) includes at least one tissue-spacer 30 to help prevent the magnet $15m$ from contacting local tissue until the magnet $15m$ is in a desired position or in a desired alignment with the magnet $15m$ held by the other catheter. The tissue-spacer 30 can project outwardly about an entire perimeter, e.g., the entire circumference (FIG. 5), or about a portion of the perimeter (FIG. 11B), and may project beyond the tip (FIG. 16). As shown in FIG. 5, the catheter 20 can include at least two tissue-spacers 30. The tissue-spacers 30 can be configured as a pair $30_1$, $30_2$, one on each side of the deployment window 40, but one or more than two tissue spacers 30 may also be used. FIG. 6A illustrates that catheter 10 can have this tissue-spacer configuration while catheter 20 is devoid of any tissue-spacers. The catheters can be configured in the opposite manner. Alternatively, FIG. 6B illustrates that both catheters 10, 20 have the tissue spacers 30.

Figure 15:
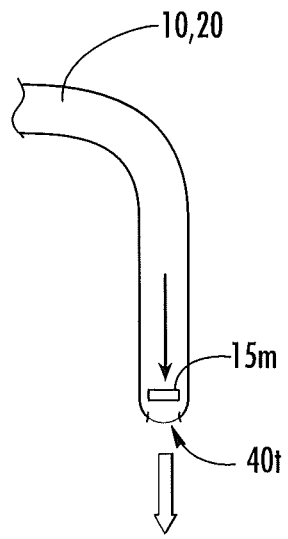
FIG. 15 is a schematic illustration of a catheter configured to deploy a magnet via the tip according to embodiments of the present invention.
Figure 17:
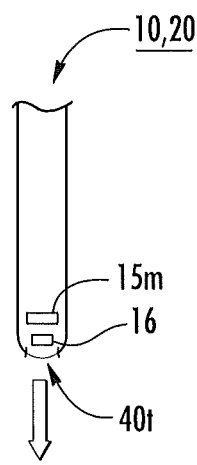
FIG. 17 is a schematic illustration of a catheter configured to deploy a magnet via the tip and deliver mucosal cells according to some embodiments of the present invention.

FIGS. 15-17 illustrate examples of catheters with tip deployment windows $40t$. The magnet $15m$ can be ejected or deployed from a tip window $40t$ rather than from a side exit window. The tip window $40t$ can be configured similar to the deformable window discussed above with respect to FIGS. 12A and 12B but can cooperate with an axially sliding pusher or other expulsion member or configuration (pressurized fluid, a biasing member (compressed resilient member or spring), and the like). FIG. 16 illustrates that an inflatable tissue spacer $30b$ can be used with the tip window $40t$. The spacer $30b$ can be configured to expand sufficiently to extend beyond the tip $40t$. FIG. 17 illustrates that the catheter 10, 20 may also place mucosal cells 16 proximate the target site, typically in advance of the magnet compression to trap the cells during the compression to improve patentcy.

The tissue-spacer 30 is configured to extend a distance out beyond the bounds of the catheter body to space the magnet $15m$ away from local tissue, then retract to allow the body of the catheter 10, 20 to be closer to target tissue for deployment of the magnet 15m from the catheter window 40. The tissue spacers 30 can be a fin, finger, or other member that can space the catheter body apart from tissue, then controllably retract into or against the body of the catheter. However, in particular embodiments, the tissue-spacer 30 comprises an inflatable balloon 30b (that is also deflatable). Partial or total deflation can be used when the magnet 15m is aligned with the opposing magnet 15m across a target tissue barrier. Where more than one inflatable tissue-spacer 30b is used, it can be concurrently or independently inflated and/or deflated during use. The balloons 30b can be configured to inflate outwardly between about 1 mm to about 1 cm, typically between about 5 mm to about 50 mm, and more typically between about 10 mm to about 20 mm, to provide a corresponding amount of spacing from local tissue.

The catheters 10, 20 can be positioned in the body with the tissue-spacers 30 retracted/deflated or extended/inflated, depending on the intrabody path to the desired location. However, as a catheter 10, 20 approaches a desired location or once in the body passage that has sufficient clearance, the tissue spacer 30 can be expanded or extended. The magnet 15m can be held in the window 40 or held retracted inside the channel 60 a distance away from the window 40 during placement to the target site in the body. When the alignment and/or position is confirmed as correct or appropriate (via an imaging modality such as ultrasound and/or fluoroscopy or based on force measurements of the attractant force of the two magnets), the tissue-spacer(s) 30b can be deflated and the magnet 15m deployed from the window 40, thereby positioning the magnet 15m in a desired aligned position. The inflatable/deflatable tissue-spacer 30 can have any desired inflated shape. In some embodiments, the inflatable spacer 30b can have a bulbous balloon-like shape as shown in FIG. 5 or a substantially constant annular shape (FIG. 6B). In other embodiments as shown in FIG. 6C, the inflatable tissue spacer 30b can extend about a portion of a transverse cross-section, typically on the same side as the window exit 40.

Referring to FIG. 5, the catheters 10, 20 can include a magnet pusher 45 or other magnet deployment member that can expel and/or movably position the magnet to exit the catheter window 40. In some embodiments, the catheter 10, 20 can include an inwardly extending shoulder 66 (e.g., crimp, resilient fins or fingers, or ledge) that acts as a stop to inhibit early deployment. The shoulder 66 can reside upstream of the window 40 but is typically proximate the window to limit actuation distance of the pusher. However, the magnet 15m can be locked at a desired position using string or other locking configurations and a retaining shoulder is not required.

Figure 14A:
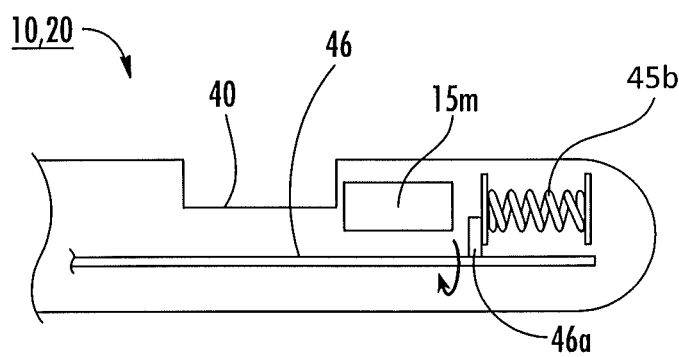
FIGS. 14A and 14B are schematic illustrations of a distal portion of a catheter having a biasing (compressed) member that can push the magnet into a delivery window according to embodiments of the present invention.
Figure 14B:
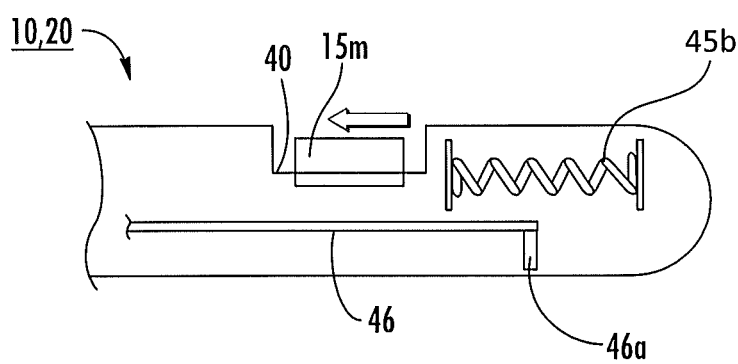

The pusher 45 is configured to push the magnet out of the catheter 10, 20. The pusher 45 can be an elongate member that can be slidably advanced in the 5b channel 60 of the catheter 10, 20 to physically push the magnet toward the window 40 (and beyond the shoulder 66, where used). As shown in FIGS. 14A and 14B, the magnet pusher 45 may alternatively or additionally include a biasing member 45b, such as a spring or elastic compressed resilient member, that can be released or unbound to expand to force the magnet forward or rearward (the latter if held distal to the window) toward the window 40. In one embodiment, the biasing member 45b is held distal of the magnet 15m in the catheter in a compressed state (FIG. 14A) by an elongate member 46 having an arm 46a. Turning the elongate member 46 turns the arm 46a outwardly and releases a proximal end of the biasing member 45b, which expands to force the magnet 15m to enter the window 40. Pressurized fluid can also or alternatively be used to force the magnet to exit the window 40 (not shown).

FIG. 7 illustrates a section view of an exemplary catheter 10, 20. As shown, the catheter 10, 20 includes a channel 60 that can hold the magnet 15m and/or pusher 45. At least one fluid path 65 extends from a proximal end of the catheter to the inflatable balloon 30b inside the catheter body and along a length thereof (typically as a longitudinal channel formed through a thickness of an outer wall) of the catheter. Alternatively, the fluid path 65 can be formed using at least one discrete tube that resides in the channel 60 to inflate the spacer 30b (where an inflatable version is used). The inflatable balloon spacer 30b can be inflated similar to a FOLEY catheter using any suitable fluid, typically saline. Where two or more paths 65 are used, one can extend to a respective balloon spacer 30b ; both paths 65 can extend to both spacers 30b (where more than one spacer 30b is used) or multiple paths 65 can be used to inflate and/or deflate a respective spacer 30b. Alternatively, one path 65 can be an inflation path and the other can be used for deflation where the fluid is desired to remain captured and not released in the patient (at least at the magnet site). As yet another alternative, a two-way valve can be used to allow the same path to be used for inflation and deflation.

The magnet 15m can have any suitable configuration, but generally has a length dimension that is greater than the width or radius. The magnet 15m can be sterile (sterilized by any appropriate means suitable for medical use) and held in a sterile package 150 for medical use (FIGS. 8, 9). The magnet 15m can be held in a flexible container (typically with insulators such as foam packing or other material that inhibits breakage during shipment) and/or may be included with a catheter as a kit or packaged in other suitable configurations. The term "sterile" refers to devices that meet cleanliness standards guidelines for human and/or animal surgical uses (e.g., FDA guidelines in the U.S.). FIG. 8 illustrates two exemplary shapes: a relatively thin polygon shape and a cylinder. The magnets 15m can be sized and configured to form a desired anastomosis size (and/or to accommodate the passage to the target site). They should have sufficient magnetic strength to apply sufficient compressive force to form an ischemic anastomosis (when used for this purpose). The magnets 15m can vary in length depending on the end use, but are typically between about 0.5 mm-2 mm long and between about 0.1-3 mm in width or diameter. The slit (e.g., opening) formed by the magnetic compression is typically about two times the length of the magnet 15m. For example, for certain embodiments, the magnets 15m can form a hole such as between about 1 mm-10 mm across, typically about 2 mm wide and up to about 25 mm long. In particular embodiments, the magnets 15m can be sized and configured to create small linear openings such as between about 1-2 mm wide and up to about 25 mm long (this size may be particularly suitable for the ureter).

The magnet 15m can comprise a rare earth magnet, which is typically much stronger than a ferrous magnet. There are two conventional types of rare earth magnets, neodymium magnets (e.g., neodymium-iron-boron) and samarium-cobalt magnets. Rare earth magnets can be extremely brittle and can also be vulnerable to corrosion (such as from the digestive acids in the body). The magnets 15m can be plated or coated with a biocompatible material such as silicone to protect them from breaking, chipping and/or for corrosion resistance. Particular examples of rare earth magnets include $Nd_2Fe_{14}B$, $SmCo_5$ and $Sm(Co,Fe,Cu,Zr)_7$. However, it is contemplated that $Nd_2Fe_{14}B$ may be particularly suitable for some embodiments.

FIG. 5 also illustrates that at least one string 62 can be attached to the magnet 15m to allow for retrieval, in some embodiments. The string 62 can reside outside the pusher member 45 as shown or extend through an axially extending slot or channel formed on an exterior wall of the pusher or formed through a center or other interior location of the pusher body. The string 62 can be detachable from the magnet 15m, once in position in the body, or may remain on the magnet 15m. Alternatively or additionally, the string 62 may be resorbable, depending on the end use.

FIG. 9 illustrates that one or both magnets 15m can include a radioactive material 50. The term "radioactive material" refers to any suitable radioactive emitter material that can be placed onto or into the magnet or other target device. The radioactive material may provided to the magnet 15m (or substrate forming part of the magnet assembly) in any manner, such as in a laminated over-layer, a laminated sub-surface layer, a coating, sputter-deposition, and the like. The radioactive material can be a beta emitter, such as strontium-90, carbon-14, tritium, Yttrium-90 and sulfur-35. In particular embodiments, the radioactive material comprises Yttrium-9Q, which has a relatively small penetration depth, e.g., about 2 mm, average to about 10 mm, average (max). The radioactive material may also comprise an alpha emitter such as radium, radon, uranium, or thorium, as such may also be able to provide a small penetration depth. In some embodiments, the cooperating magnets 15m with at least one of the magnets 15m having the radioactive material 50 configured to face the other magnet 15m can generate compression and use the radiation to act as an "atomic knife" to facilitate a clean and relatively fast anastomosis. The radioactive material 50 may be selected to have a relatively short half-life, e.g., less than about two weeks (Yittrium-90 has a half-life of about 64 hours).

The material 50 can be formed on one surface integrated into a subsurface region or be placed on the entire perimeter. It is contemplated that by selectively placing the material 50 on one surface, this surface can be held enclosed in the catheter until the magnet is in a desired location, then rotated to face out the window 40 and deployed. This can limit exposure to non-target tissue. The magnet 15m can be oriented so that the side, surface or interior having the radioactive material 50 faces and is held against the tissue using the magnetic compression to create the anastomosis.

The catheter 10, 20 can have spaced apart inflatable spacers 30b about each window 40 that can be separately inflated or deflated to help place the magnets 15m in a desired location. FIG. 12 shows the more proximal inflatable spacers 30b in a deflated or partially deflated state while the more distal inflatable spacers are inflated.

Figure 11A:
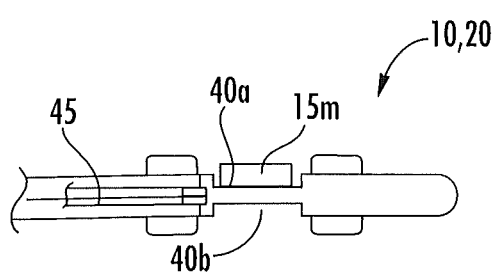
FIGS. 11A and 11B are schematic illustrations of catheters that hold a magnet in a stored enclosed position for subsequent placement via an exit window to place a magnet according to embodiments of the present invention.
Figure 11B:
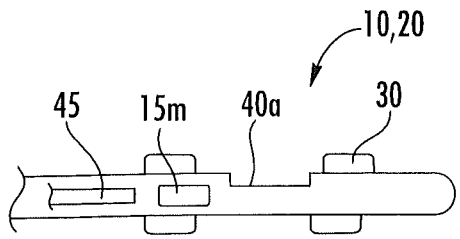

The window 40 can be a laterally extending window on one side of the catheter 10, 20 (FIG. 5) or may extend substantially about the entire perimeter. Alternatively, the window 40 can be configured to have circumferentially spaced apart window panels 40a, 40b (FIG. 11A) for selective deployment of the magnet 15m from one. The window panels 40a, 40b may be axially offset from each other a defined distance (instead of aligned across from each other as shown in FIG. 11A), such as between about 10%-200% of a length of the magnet 15m. In yet other embodiments, the exit window 40 may be located on an end of the catheter rather than along a side.

Figure 12A:
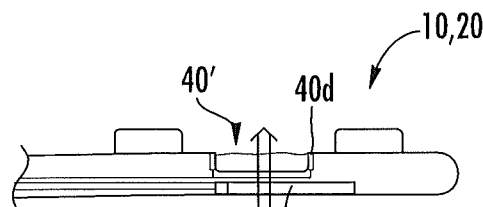
FIG. 12A is a schematic illustration of a catheter with a magnet held in an exit window that is deformable to release and place a magnet held according to embodiments of the present invention.
Figure 12B:
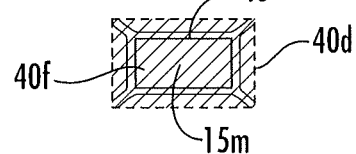
FIG. 12B is a top view of an exemplary deformable window for the catheter of FIG. 12A according to embodiments of the present invention.
Figure 12C:
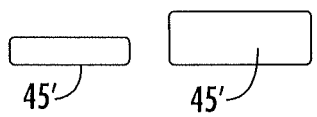
FIG. 12C is a schematic side view of an inflatable member that can be used to force the magnet out of the deformable window of FIG. 12A according to embodiments of the present invention.

Referring to FIGS. 12A and 12B, in some embodiments, the window 40' can have a deformable outer perimeter 40d. For example, the window 40' can have a scored or preferentially weaker boundary that when pushed with sufficient pressure/force allows the underlying magnet to pass therethrough. The window 40' can have a size in the non-deformed shape that is less than that of the magnet body. In this configuration, the magnet 15m may be held under the window 40 during insertion of the catheter in the body. The magnet 15m can be pushed out of the window by pushing out the deformable perimeter 40d of the window. FIG. 12C illustrates that the pusher 45' can include an inflatable end portion that expands to push the magnet 15m out the window 40'.

In some embodiments, the magnet and/or catheter can be configured to introduce a therapeutic agent 40f. For example, the window 40, 40' can have a thin film biocompatible material (e.g., thin film or cover) 40f that extends over the open space used to expel or deploy the magnet 15m. The thin film 40f can be a restorable, dissolvable biocompatible material that can be released from the catheter body and held on a surface of the magnet 15m. In some embodiments, the material can be a therapeutic agent configured as an outer coating on the magnet body or may be embedded in an intermediate layer of the magnet body. The material 40f can be configured to inhibit scar and/or collagen formation and/or promote mucosal tissue growth about the anastomosis. The material 40f can comprise stem cells and/or mucosal cells to promote mucosal tissue growth that are released to local tissue during the magnetic compression. FIG. 17 shows that the catheter rather than the magnet can include a therapeutic agent (e.g., eject locally) before, after or during deployment of the magnet 15m. The covering 40f may help with corrosion issues and/or provide cushioning during deployment of the magnet 15m. The mucosal cells may improve patency. The catheter and/or magnet can be configured to provide a time-released medicament such as one or more of: an anti-scarring agent, a mucosal tissue growth promoter, an antibiotic, an anti-inflammatory or other agent.

Figure 10:
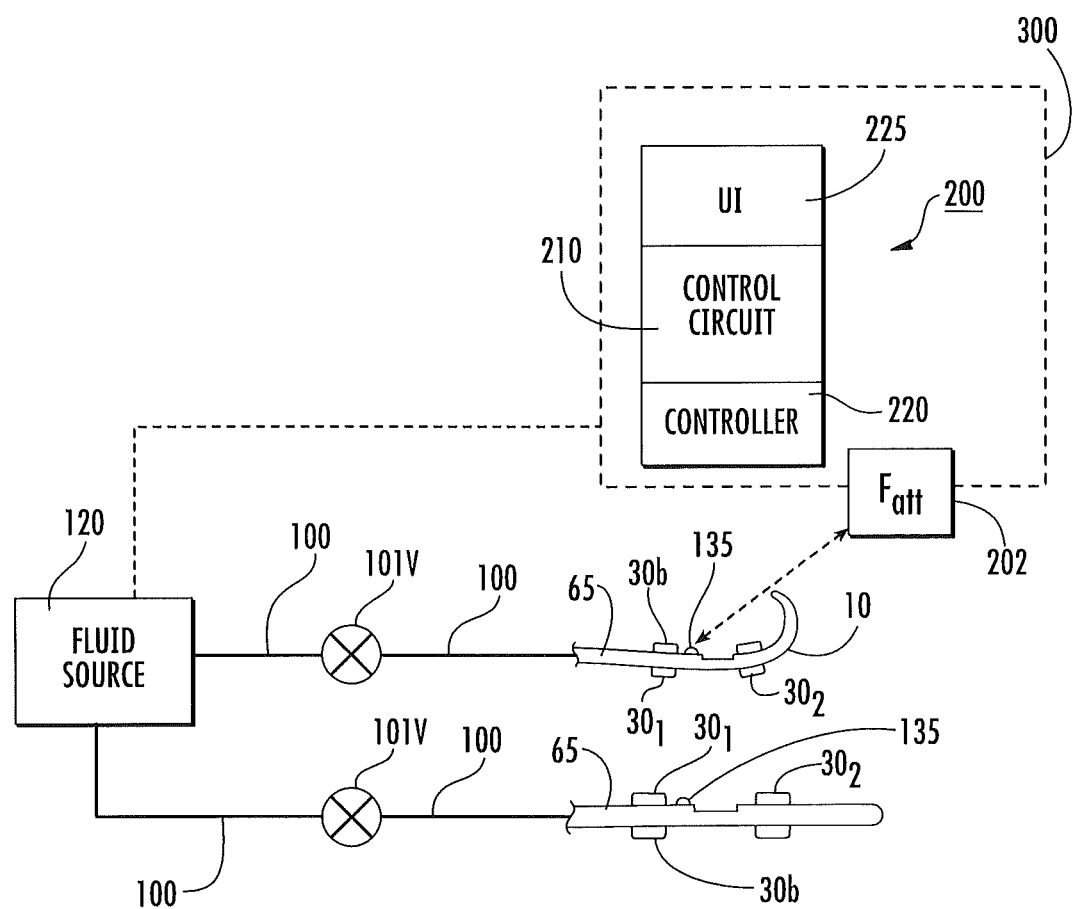
FIG. 10 is a schematic illustration of a system for delivering intrabody magnets using inflatable/deflatable spacers according to embodiments of the present invention.

FIG. 10 is a schematic illustration of a system 200 used with one or more catheters 10, 20 with fluid paths 65 in fluid communication with the inflatable spacers 30b (both shown having at least two $30_1$, $30_2$) on one end and conduits/tubing 100 on the other that connect to a fluid source 120. The fluid source and associated flow paths 100 can include one or more valves for inflating and/or deflating the spacers 30b. The system 200 can include a control circuit 210 with a controller that directs the inflation/deflation upon instructions from a user (such as a surgeon). The circuit 210 can have a User Interface 225 such as an HMI that allows the surgeon to indicate when to inflate and deflate the spacers 30b. Of course, the catheters 10, 20 may also or alternatively allow manual direction of activation controls for this purpose. The fluid source 120 can have flow meters that can control flow rates. The control circuit 200 can be hard wired to the fluid source or may wirelessly communicate with one or all the system components to direct the inflation and deflation. The control circuit 200 can be configured with a force monitoring module 202 to monitor attractant force using a force sensor 135 on one (typically both) catheters 10, 20, proximate the window 40, 40'. It is contemplated that if tissue at a local site is too thick (e.g., greater than about 1 cm) and/or the magnetic strength is not sufficiently strong, an incomplete or unsuitable anastomosis may be formed (if formed at all, at least without the radioactive material). While the tissue thickness may be measured using an imaging modality, in some embodiments, one or both catheters 10, 20 can include a force sensor 135 that also or alternatively measures a magnetic attraction force generated when the two magnets 15m are proximate to each other. This force may be measured once when at least one of the two magnets 15m is in position outside a respective catheter body. In some embodiments, the force can be monitored once both magnets 15m are at least partially deployed so that they are held together to apply magnetic compression. Alternatively, the force can be measured prior to actual deployment of either magnet (such as while a spacer is at least partially inflated). The system 10 can be configured to lock release of the magnet 15*m* based on a threshold force required before allowing deployment. The force between the two magnets 15*m* depends on the strength and orientation of both magnets and the distance (tissue thickness) and direction of the magnets relative to each other. The force is sensitive to rotations of the magnets due to magnetic torque. The force on each magnet depends on its magnetic moment and the magnetic field B of the other. The force sensor 135 can be configured as a wire or any suitable sensor configuration.

Figure 13:
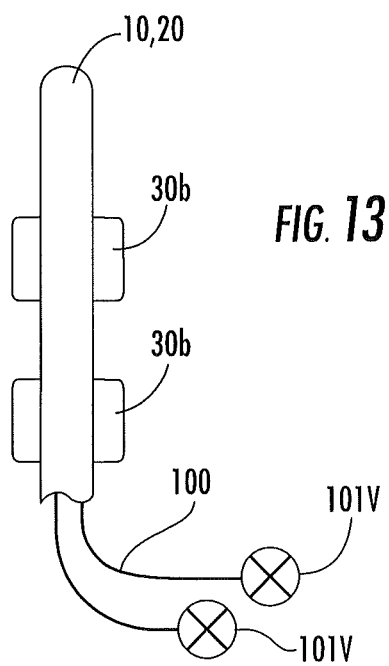
FIG. 13 is a schematic illustration of a catheter with at least two inflatable members and corresponding fluid paths and valves according to embodiments of the present invention.

FIG. 10 illustrates one conduit 100 that is in communication with a fluid path 65 of a spacer(s) 30*b*. FIG. 13 is a schematic illustration of a catheter 10, 20 that can have at least two inflatable members 30*b* and a corresponding at least two fluid paths 65, at least two conduits 100 and valves 101 according to embodiments of the present invention.

The circuit 200 can include a digital signal processor and/or an Application Specific Integrated Circuit (ASIC) (e.g., ASIC and/or processor with software) that includes or executes part or all of the computer readable program code for generating the inflation/deflation directions, responding to input from the UI 225, and monitors force 202. The circuit 200 can include a data processing system which may, for example, be incorporated or integrated into the processor. The processor can communicate with or include electronic memory. The processor can be any commercially available or custom microprocessor. The memory is representative of the overall hierarchy of memory devices containing the software and data used to implement the functionality of the data processing system. The memory can include, but is not limited to, the following types of devices: cache, ROM, PROM, EPROM, EEPROM, flash memory, SRAM, and DRAM.

The processor or memory may include several categories of software and data used in the data processing system: the operating system; the application programs; the input/output (I/O) device drivers; and tension data.

As will be appreciated by those of skill in the art, the operating systems may be any operating system suitable for use with a data processing system, such as OS/2, AIX, or zOS from International Business Machines Corporation, Armonk, N.Y., Windows CE, Windows NT, Windows95, Windows98, Windows2000, WindowsXP, Windows Visa, Windows7, Windows CE or other Windows versions from Microsoft Corporation, Redmond, Wash., Palm OS, Symbian OS, Cisco IOS, VxWorks, Unix or Linux, Mac OS from Apple Computer, LabView, or proprietary operating systems. The I/O device drivers typically include software routines accessed through the operating system by the application programs to communicate with devices such as I/O data port(s), data storage and certain memory components. The application programs are illustrative of the programs that implement the various features of the data processing system and can include at least one application, which supports operations according to embodiments of the present invention. The data represents the static and dynamic data used by the application programs, the operating system, the I/O device driver and the like.

The control circuit 210 and/or UI 225 of the system 200 can wirelessly communicate with a clinician workstation 300 and/or other remote computer device or may be integrated into the clinician workstation 300. The system 200 and/or workstation 300 can include a display that can communicate with a computer which includes a portal and an Application that allows the force data to be graphically displayed for a patient record or other data record. The system or components thereof can communicate with the workstation or other remote device via a computer network including an intranet or the internet with the appropriate use of firewalls for patient privacy and compliance with HIPPA (Health Insurance Portability and Accountability Act) or other regulatory rule or authority.

The system 200 can include an electronic library of target forces correlated to separation distance, such as target force ranges per distance separation (e.g., 1 mm, 2 mm, 3 mm) that can be used to identify a desired threshold force for surgical use/referral. This can help a clinician decide whether to retrieve or deploy a magnet or change a site. The force/distance data can be generated using tissue phantoms and force curves based on magnet type, for example.

Turning again to FIGS. 3A-3B, in some embodiments, robotic members can deliver the magnets and may not require the use of catheters 10, 20 to place a respective magnet 15*m* for creating the linear ischemic injury. In any event, the pair of magnets 15*m* can be used to create the first/primary anastomosis during the connection of the ureter to the ileal conduit.

In some embodiments, the first catheter 10 can be inserted percutaneously into the ureter and guided down to the ileal conduit using conventional needle-guidewire-dilator techniques and local anesthesia. The second catheter 20 can be inserted into the ileal conduit via a trans-ileal conduit entry from the stoma. The intrabody placements of the distal end portions of the catheters 10, 20 can be carried out using an imaging modality such as ultrasound and/or fluoroscopy, or, as needed, a laproscopy, as is well known. The inflatable tissue spacers 30*b* can be expanded (either before or as the window 40 approaches the magnet/window of the first catheter 10) on the other side of the tissue. When the magnet 15*m* is configured to be in the desired location and in alignment with the other magnet 15*m*/window 40, the tissue spacers 30*b* can be deflated, which allows the catheter body to move closer the wall and positions the window 40 closer to the target tissue. The magnet 15*m* can be deployed to form a compressive lock against the other magnet 15*m* on the other side of the tissue. If a clinician/surgeon decides that the placement is not optimum or proper, the spacers 30*b* can be re-inflated and the window repositioned. If the magnet 15*m* has been deployed out of the window, then it may be pulled back in via string 62. In some embodiments, the magnetic force can be measured with an onboard sensor 135 (FIG. 10) if, for example, the gall bladder wall is too thick (as determined by a reduced force), the magnet 15 may not be deployed, and/or an alert can be generated so that a clinician can make appropriate adjustments. Once deployed, the magnets 15*m* generate magnetic compression on the tissue and can form an anastomosis over time. The magnets 15*m* are subsequently passed through the formed opening into the and out of the body via the stoma.

It is noted that while embodiments of the invention are particularly suitable for ureter to illeal conduit uses, other uses are possible including, for example, biliary uses.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, if used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A ureter catheter, comprising:
a catheter body sized and configured to travel through a ureter of a patient, the catheter body having an inner channel and an outer wall enclosing the inner channel, wherein the catheter body comprises at least one inflatable tissue spacer proximate a magnet exit window, wherein the magnet exit window is an open space in the outer wall of the catheter body that is spaced apart from a tip of the catheter body, the at least one inflatable tissue spacer having an inflated configuration during intrabody placement of the catheter body, wherein the at least one inflatable tissue spacer is disposed on and extends laterally outward from the outer wall of the catheter body, the at least one inflatable tissue spacer is affixed to the catheter body to reside at a fixed longitudinal position relative to the catheter body while being able to laterally expand and retract; and
a first rare earth magnet releasably held in the catheter body adapted for positioning in a distal end of the ureter proximate an ileal conduit, wherein the first rare earth magnet is elongate and has a length dimension that is greater than a width dimension or radius and is releasably held in the inner channel of the catheter body separate from the at least one tissue spacer to exit from the magnet exit window after the at least one inflatable tissue spacer is at least partially deflated to position the magnet exit window adjacent the ileal conduit and closer to target tissue of the ileal conduit than when the at least one tissue spacer is in the inflated configuration, and wherein, in position in the distal end of the patient ureter, the first rare earth magnet is configured to cooperate with a second rare earth magnet on an opposing side of the target tissue to form a linear compression anastomosis.

2. A method of forming an anastomosis using the device of claim 1, comprising:
placing the catheter of claim 1 with the first elongate rare earth magnet in a ureter of a patient proximate target tissue in an ileal conduit while the at least one inflatable tissue spacer is inflated;
placing the second elongate rare earth magnet in the ileal conduit of a patient proximate the ureter before, during or after the placing of the first catheter with the first elongate rare earth magnet;
deflating the at least one inflatable tissue spacer to position the first elongate rare earth magnet in the catheter closer to the target tissue relative to its spacing while the at least one inflatable tissue spacer is inflated; then
releasing the first elongate rare earth magnet from the magnet exit window of the catheter while the at least one inflatable tissue spacer is deflated; then
compressing tissue trapped between the first and second rare earth magnets based on a magnetic attraction force generated by the magnets, the compressing performed with sufficient force to form an anastomosis.

3. The method of claim 2, wherein the deflating step is carried out after the first rare earth magnet is in cooperating alignment with the second rare earth magnet, and wherein the placing steps are carried out to create a side-to-side anastomosis upstream of an original anastomosis or a sutured end Of the ureter.

4. The method of claim 2, wherein at least one of the first and second rare earth magnets comprises a radioactive material, the method further comprising exposing the trapped tissue to radiation from the at least One rare earth magnet with the radioactive material, wherein the forming step is carried out based on the compressing and the exposing steps.

5. The ureter catheter of claim 1, wherein the at least one inflatable tissue spacer comprises a first inflatable tissue spacer proximate one end of the magnet exit window and a second inflatable tissue spacer proximate an opposing longitudinal end of the magnet exit window, and wherein the inflatable tissue spacers are configured to be concurrently deflated prior to releasing the first rare earth magnet from the magnet exit window.

6. The ureter catheter of claim 1, wherein the first rare earth magnet comprises neodymium.

7. The ureter catheter of claim 1, wherein the first and/or second rare earth magnet comprises a radioactive material.

8. The ureter catheter of claim 7, wherein the radioactive material comprises a beta emitter having a half-life that is between about 24 to about 120 hours.

9. The ureter catheter of claim 7, wherein the radioactive material comprises Yttrium-90.

10. The ureter catheter of claim 1, further comprising a magnetic force sensor held by the catheter body proximate the magnet exit window, wherein the magnetic force sensor is configured to provide force data associated with magnetic attraction force of the first rare earth magnet with the second rare earth magnet used to generate the linear compression anastomosis before the first rare earth magnet is released from the catheter body.

11. The ureter catheter of claim 1, wherein the first rare earth magnet has a solid elongate cylindrical body.

12. The ureter catheter of claim 1, wherein the first rare earth magnet has a solid elongate polygon body.

13. The ureter catheter of claim 11, wherein the first rare earth magnet has a diameter that is between about 0.1 mm to about 3 mm in width or diameter.

14. The ureter catheter of claim 1, wherein the first rare earth magnet is rectangular.

15. The ureter catheter of claim 1, wherein the first rare earth magnet and the second rare earth magnet form a slit due to the linear compression anastomosis that is between about 1 mm to about 10 mm across and about 25 mm long.

16. The ureter catheter of claim 1, wherein the first rare earth magnet is adapted to be discharged from a patient body in urine after the anastomosis is formed.

17. The ureter catheter of claim 1, wherein the catheter further comprises a magnetic force sensor on the catheter body proximate the magnet exit window, and wherein the magnetic force sensor is configured to provide force data associated with a magnetic attraction force of the first rare earth magnet with the second rare earth magnet used to generate the linear compression anastomosis, and wherein the magnet force, sensor obtains the force data as the at least one inflatable tissue spacer is deflated to thereby facilitate proper positioning of the first rare earth magnet in the patient prior to deploying the first rare earth magnet from the catheter body.

18. A ureter catheter, comprising:
a catheter body sized and configured to travel through a ureter of a patient, the catheter body having an inner channel and an outer wall enclosing the inner channel, wherein the catheter body comprises at least one inflatable tissue spacer proximate a magnet exit window, the at least one inflatable tissue spacer having an inflated configuration during intrabody placement of the catheter body; and a first rare earth magnet releasably held in the catheter body adapted for positioning in a distal end of the ureter proximate an ileal conduit, wherein the first rare earth magnet is elongate and has a length dimension that is greater than a width dimension or radius and is releasably held in the inner channel of the catheter body to exit from the magnet exit window after the at least one inflatable tissue spacer is at least partially deflated to position the magnet exit window adjacent the ileal conduit and closer to target tissue of the ileal conduit than when the at least one tissue spacer is in the inflated configuration, and wherein, in position in the distal end of the patient ureter, the first rare earth magnet is configured to cooperate with a second rare earth magnet on an opposing side of the target tissue to form a linear compression anastomosis, wherein the catheter body magnet window is a tip exit window, wherein the at least one inflatable tissue spacer is affixed to and external of the outer wall of the catheter body and can inflate outwardly away from the catheter body about the magnet exit window, and wherein the magnet exit window is configured to place the first rare earth magnet on a sidewall of the ureter facing the ileal conduit to form a side-to-side anastomosis.

19. A catheter, comprising:

a catheter body sized and configured to travel through a stoma and a distance through an ileal conduit of a patient, the catheter body having an inner channel and an outer wall enclosing the inner channel, wherein the catheter body comprises a longitudinally extending magnet exit window extending through the outer wall having opposing first and second ends extending a defined length of the catheter body spaced apart from a tip of the catheter body, and a first inflatable tissue spacer residing proximate the first end of the magnet exit window and a second inflatable tissue spacer residing proximate the second end of the magnet exit window wherein the first and second inflatable tissue spacers are disposed on and external to the outer wall of the catheter body and are configured to inflate laterally outward a distance beyond the outer wall of the catheter body; and a first rare earth magnet having an elongate body with a length dimension that is greater than a width dimension or radius and is releasably held in the inner channel of the catheter body adapted for release through the magnet exit window only after deflation of the first and second tissue spacers to move the magnet exit window closer to target tissue at the ileal conduit proximate a ureter relative to when the tissue spacers are inflated, wherein, in position in the ileal conduit, the first rare earth magnet is configured to cooperate with a second rare earth magnet to form a linear compression anastomosis, wherein, in the catheter body, the first rare earth magnet can slidably extend in a longitudinal direction through the catheter body inner channel while the tissue spacers remain affixed to the catheter body proximate the magnet exit window.

20. The catheter of claim 19, wherein the first rare earth magnet comprises neodymium.

21. The catheter of claim 19, wherein the first and/or second rare earth magnet comprises a radioactive material.

22. The catheter of claim 21, wherein the radioactive material comprises a beta emitter having a half-life that is between about 24 to about 120 hours.

23. The catheter of claim 21, wherein the radioactive material comprises Yttrium-90.

24. The catheter of claim 19, wherein the catheter further comprises a magnetic force sensor on the catheter body proximate the magnet exit window, and wherein the magnetic force sensor is configured to provide force data associated with a magnetic attraction force of the first rare earth magnet with the second rare earth magnet used to generate the linear compression anastomosis before the first rare earth is released from the magnet exit window.

25. The catheter of claim 19, wherein the first rare earth magnet has a solid elongate cylindrical body.

26. The catheter of claim 19, wherein the first rare earth magnet has a solid polygonal shaped body.

27. The catheter of claim 26, wherein the first rare earth magnet has a short dimension that is between about 0.1 mm to about 3 mm in width or diameter.

28. The catheter of claim 19, wherein the first rare earth magnet is rectangular and has a width between about 0.1 mm to about 3 mm.

29. The catheter of claim 19, wherein the first rare earth magnet is configured to cooperate with the second rare earth magnet to form a slit due to the linear compression anastomosis that is between about 1 mm to about 10 mm across and about 25 mm long.

30. The catheter of claim 19, wherein the first and second rare earth magnets are adapted to be discharged from a patient body in urine after the anastomosis is formed.

31. The catheter of claim 19, wherein the catheter further comprises a magnetic force sensor on the catheter body proximate the magnet exit window, and wherein the magnetic force sensor is configured to provide force data associated with a magnetic attraction force of the first rare earth magnet with the second rare earth magnet used to generate the linear compression anastomosis, and wherein the magnet force sensor obtains the force data as the inflatable tissue spacers are deflated to thereby facilitate proper positioning of the first rare earth magnet in the patient prior to deploying the first rare earth magnet from the catheter body.

* * * * *